US011339137B2

(12) United States Patent
Farida et al.

(10) Patent No.: US 11,339,137 B2
(45) Date of Patent: May 24, 2022

(54) METHOD FOR PRODUCING 3,4-DICHLORO-N-(2-CYANOPHENYL)-5-ISOTHIAZOLECARBOXAMIDE

(71) Applicants: Bayer Aktiengesellschaft, Leverkusen (DE); Bayer CropScience Aktiengesellschaft, Monheim am Rhein (DE)

(72) Inventors: Taraneh Farida, Pulheim-Geyen (DE); Martin Littmann, Leverkusen (DE); Ali Sanli, Leverkusen (DE); Kyra Larissa Pabst, Cologne (DE); Juergen Ludwig, Odenthal (DE); Albert Schnatterer, Leverkusen (DE)

(73) Assignees: Bayer Aktiengesellschaft, Leverkusen (DE); Bayer CropScience Aktiengesellschaft, Monheim am Rhein (DE)

( * ) Notice: Subject to any disclaimer, the term of this patent is extended or adjusted under 35 U.S.C. 154(b) by 0 days.

(21) Appl. No.: 17/045,069

(22) PCT Filed: Apr. 2, 2019

(86) PCT No.: PCT/EP2019/058245
§ 371 (c)(1),
(2) Date: Oct. 2, 2020

(87) PCT Pub. No.: WO2019/192988
PCT Pub. Date: Oct. 10, 2019

(65) Prior Publication Data
US 2021/0163430 A1    Jun. 3, 2021

(30) Foreign Application Priority Data
Apr. 6, 2018  (EP) .................... 18166110

(51) Int. Cl.
*C07D 275/03*     (2006.01)
(52) U.S. Cl.
CPC ................ *C07D 275/03* (2013.01)

(58) Field of Classification Search
CPC .................................................. C07D 275/03
See application file for complete search history.

(56) References Cited

U.S. PATENT DOCUMENTS

| 6,277,791 | B1 | 8/2001 | Assmann et al. |
| 6,372,692 | B1 | 4/2002 | Assmann et al. |
| 6,642,181 | B2 | 11/2003 | Assmann et al. |
| 6,875,783 | B2 | 4/2005 | Assmann et al. |
| 7,157,481 | B2 | 1/2007 | Assmann et al. |
| 7,696,355 | B2 | 4/2010 | Assmann et al. |
| 2002/0091067 | A1 | 7/2002 | Assmann et al. |
| 2004/0044054 | A1 | 3/2004 | Assmann et al. |
| 2005/0159464 | A1 | 7/2005 | Assmann et al. |
| 2007/0232670 | A1 | 10/2007 | Assmann et al. |

FOREIGN PATENT DOCUMENTS

| CN | 102942565 | * | 2/2013 |
| CN | 102942565 | A | 2/2013 |
| WO | 99/24413 | * | 5/1999 |
| WO | 9924413 | A2 | 5/1999 |
| WO | 2004002968 | A1 | 1/2004 |

OTHER PUBLICATIONS

ChemEurope.Com news article 120244, dated Jul. 20, 2010, http://www.chemeurope.com/en/news/120244/ . (Year: 2010).*
International Search Report for Application No. PCT/EP2019/058245 dated May 15, 2019.

* cited by examiner

*Primary Examiner* — D Margaret M Seaman
(74) *Attorney, Agent, or Firm* — McBee Moore & Vanik IP, LLC

(57) ABSTRACT

The present invention relates to a novel, one-stage method for preparing and isolating 3,4-dichloro-N-(2-cyanophenyl)-5-isothiazolecarboxamide (isotianil), which has microbicidal and plant-fortifying (host defence inducer) properties. In the method according to the invention, the amount of waste from the production process (e.g. solvent) is significantly reduced. The product is provided in high yield and purity (minimal amount of by-products and impurities). Compared to existing preparation methods, the method according to the invention has the advantage of low corrosiveness and high yield and high selectivity.

15 Claims, No Drawings

METHOD FOR PRODUCING 3,4-DICHLORO-N-(2-CYANOPHENYL)-5-ISOTHIAZOLECARBOXAMIDE

CROSS-REFERENCE TO RELATED APPLICATIONS

This application is the National Stage entry of International Application No. PCT/EP2019/058245, filed 2 Apr. 2019, which claims priority to European Patent Application No. 18166110.9, filed 6 Apr. 2018, the content of which is hereby incorporated by reference in its entirety.

BACKGROUND

Field

The present invention relates to a novel, one-stage method for preparing and isolating 3,4-dichloro-N-(2-cyanophenyl)-5-isothiazolecarboxamide (isotianil), which has microbicidal and plant-fortifying (host defence inducer) properties. In the method according to the invention, the amount of waste from the production process (e.g. solvent) is significantly reduced. The product is provided in high yield and purity (minimal amount of by-products and impurities). Compared to existing preparation methods, the method according to the invention has the advantage of low corrosiveness and high yield and high selectivity.

Description of Related Art

The synthesis of isotianil has been described in various patent applications. For example, it is known that 3,4-dichloro-N-(2-cyanophenyl)-5-isothiazolecarboxamide of the formula (I) can be obtained by reacting 3,4-dichloroisothiazole-5-carbonyl chloride with anthranilamide in the presence of an acid acceptor and an aprotic solvent, wherein the N-[2-(aminocarbonyl)phenyl]-3,4-dichloro-5-isothiazolecarboxamide obtained from this reaction still has to be reacted in a second step with a dehydrating agent (cf. WO 2004/002968).

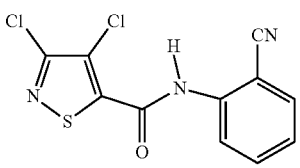

In this method, the filtrate comprises excess Vilsmeier reagent as well as $SO_2$ and hydrochloric acid (HCl), which are highly corrosive. Moreover, an aqueous work-up is described as impractical, since the N-formyl by-product is formed in significant amounts under these conditions. Furthermore, the aqueous work-up with the necessary neutralization results in an increased amount of waste.

While the non-aqueous work-up of the highly corrosive reaction mixture and isolation of the product is possible in theory, this type of work-up is not practicable however on an industrial scale and not economically viable.

It is also known that 3,4-dichloro-N-(2-cyanophenyl)-5-isothiazolecarboxamide can be obtained by reacting 3,4-dichloroisothiazole-5-carbonyl chloride of the formula (II)

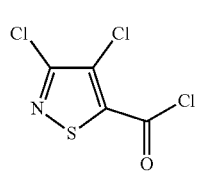

with 2-cyanoaniline (2-aminobenzonitrile) of the formula (III)

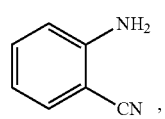

in the presence of an aprotic solvent (cf. WO 99/24413).

The method described in WO 99/24413 has the disadvantages that a large quantity of auxiliary base is required, a long reaction time is necessary, the reaction regime is complex and a high fraction of by-products is formed. Furthermore, high manufacturing costs and a comparatively large amount of wastewater are formed due to the diluted operation. (cf. Example 1 of WO 99/24413).

Accordingly, there still exists a need for an improved process which allows the preparation of 3,4-dichloro-N-(2-cyanophenyl)-5-isothiazolecarboxamide in good yield with minimal amounts of by-products and impurities, without the use of expensive solvents or solvents and residues that are difficult to manage in terms of work-up and waste treatment (e.g. $SOCl_2$ and $SO_2$). At the same time, the amount of waste per kilogram of product should be low or at least not increased compared to known methods.

When transferring reactions to an industrial scale, it is of particular importance that the reactions can also be carried out in steel reactors instead of glass vessels and, for this purpose, control of corrosive properties and a simple reaction regime is important in addition to the general reduction of waste. These factors have both economic (lower costs) and ecological effects (lower environmental impact).

Furthermore, there always exists a need for improving the space-time yield and the throughput.

SUMMARY

For this reason, the aim of the invention is to provide a method having reduced amounts of waste and tolerable corrosive properties and a simpler reaction regime, especially on an industrial scale.

The calculation of the amount of waste as described above includes not only the respective amounts of solvents, reactants and residues, but also aqueous and organic phases and the chemicals required for dilution and/or neutralization or post-treatment thereof.

Unless defined otherwise, room temperature is understood to mean a temperature of 20° C. to 22° C.

Furthermore, preferred ranges of different parameters in the present description are understood to mean that they may be freely combined, independently of the degree of preference. However, at least the combination of the most preferred configurations is understood to be a preferred embodiment of the overall process, as well as combinations of preferred ranges of equal level.

The method according to the invention is characterized by an accelerated reaction regime, minimal use of solvents and catalysts and rapid removal of corrosive reaction products such that high throughput is enabled in an operation with milder materials.

In accordance with the present invention, the method for preparing isotianil includes the steps of (a) reaction in an organic aprotic, preferably an aromatic, solvent, of 3,4-dichloroisothiazole-5-carbonyl chloride of the formula (II)

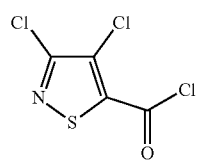

(II)

with 2-cyanoaniline (2-aminobenzonitrile) of the formula (III)

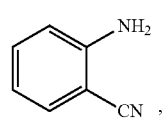

(III)

under reflux and optionally reduced pressure, and (b) filtration and washing.

DETAILED DESCRIPTION OF A PREFERRED EMBODIMENT

In step (a), preferably one of the reactants is initially charged in the solvent and heated, and the second reactant is subsequently metered in.

Step (a)

Preference is given to using non-halogenated solvents, especially aromatic solvents. The organic solvent is further preferably selected from the group consisting of benzene, toluene, o-xylene, m-xylene, p-xylene, chlorobenzene, methyl acetate, ethyl acetate, dimethylacetamide, dibutyl ether, tetrahydrofuran, methyltetrahydrofuran, dimethyl carbonate, diethyl carbonate, methyl tert-butyl ether, higher alkanes or a mixture thereof. The organic solvent is even further preferably selected from the group consisting of toluene, o-xylene, m-xylene and p-xylene. The most preferred organic solvent of the invention is toluene.

When carrying out the method according to the invention, the temperatures can be varied in a relatively broad range.

When carrying out the method according to the invention, the temperatures in step (a) are generally in the range between 20° C. and 160° C., preferably in the range of 40° C. to 120° C., more preferably in the range of 50° C. to 115° C., and most preferably in the range of 60° C. to 95° C. In a particularly preferred configuration, step (a) is carried out in a range of 70° C. to 90° C.

In the case of reaction temperatures below the boiling point of the solvent, the pressure is adjusted to the reduced temperature so that the reaction mixture boils. In this case, the boiling point increase due to dissolved reactants, reagents and products is preferably taken into consideration.

When operating at reduced pressure, the reaction temperature can be lowered and as a result a positive contribution to the energy balance is achieved. Furthermore, the reaction equilibrium can be shifted by removing volatile reaction products. As a result, the reaction time is reduced and the space-time yield is improved.

In a preferred embodiment, step (a) is carried out at 10 mbar to 700 mbar, more preferably at 150 mbar to 650 mbar, even more preferably at 150 mbar to 500 mbar, and most preferably at 200 mbar to 450 mbar, especially if toluene is used, wherein the range, also in the text below, gives the applied pressure and not the reduction of pressure starting from standard pressure. If the reaction is carried out in the range of 200 mbar to 450 mbar, the reaction temperature is preferably between 70° C. and 90° C., preferably using toluene as solvent.

However, depending on the absolute pressure and the solvent used in the method, the temperature and the pressure is adjusted by a person skilled in the art so that the desired boiling temperature is reached. Nevertheless, in order to achieve acceptable reaction times and reliable reaction conditions (e.g. not too many by-products due to thermal decomposition), the reaction temperature is preferably between 40° C. and 160° C., whereas for economic reasons (energy consumption, recovery of the solvent etc.), the reduced pressure is normally in a range of 150 mbar to 500 mbar, more preferably the temperature is between 70° C. and 90° C. and the pressure between 200 mbar and 450 mbar.

The advantages of the reaction regime under reflux are a lower fraction of by-products, a faster reaction and the recovery/removal of the outgassed hydrochloric acid.

Furthermore, in this method, it is possible to use only a minor excess or even a substoichiometric amount of the acid chloride and thus to achieve an almost ideal stoichiometry.

The ratio of aminobenzonitrile to 3,4-dichloroisothiazole-5-carbonyl chloride is preferably between 1:0.80 and 1:1.20, more preferably between 1:0.90 and 1:1.10, and particularly preferably between 1:0.95 and 1:1.04.

The amount of solvent in kg in the ratio to the reactants in kmol is preferably between 1500:1 and 100:1, more preferably between 1000:1 and 150:1, and particularly preferably between 826:1 to 238:1.

The reaction time (metered addition time plus further stirring time) is preferably between 12 h and 2 h, more preferably between 8 h and 2 h, and particularly preferably 6 h.

Step (b)

After the reaction has ended and cooling to room temperature, the precipitated product is filtered off from the reaction mixture and the filter cake is washed. The filter cake is preferably washed with an organic solvent, preferably with toluene, methanol, ethanol, isopropanol or n-propanol, particularly preferably with toluene. The filtration is preferably effected by suction filtration.

The advantages of step b) of the method according to the invention are that it is not essential to use a second solvent, and therefore no solvent mixture is formed which has to then be separated. The recovery of the solvent is therefore significantly facilitated.

The method according to the invention is characterized by a number of advantages. It enables the preparation of 3,4-dichloro-N-(2-cyanophenyl)-5-isothiazolecarboxamide (isotianil) in a very good yield and high purity, while the costs are reduced due to convenient solvents, lower proportion of solvent, fewer reagants, simpler work-up and less waste per kilogram of product, and therefore also an associated ecological effect.

The method according to the invention can be carried out without problems on an industrial scale, in addition to other reasons due to reduced corrosiveness.

The space-time throughput is improved from 20 g/l to 182 g/l in the same time period.

The amount of waste is reduced from 27.5 kg to 0.2 kg to 1.6 kg per kilogram of isotianil.

The yield increases from 89% to 98%, at a purity of 99.8%.

In a preferred configuration of the present invention, the method for preparing isotianil includes the following steps of:

(a) reaction in an organic aprotic, preferably an aromatic, solvent, of
3,4-dichloroisothiazole-5-carbonyl chloride of the formula (II)

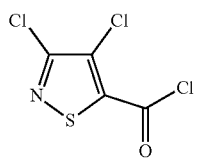

with 2-cyanoaniline (2-aminobenzonitrile) of the formula (III)

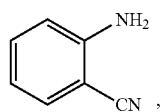

under reflux and optionally reduced pressure,
and
(b) filtration and washing,
in which the organic aprotic solvent is selected from a group consisting of benzene, toluene, o-xylene, m-xylene and p-xylene, preferably toluene, and step (a) is carried out in a range from 40° C. to 120° C. and at 150 mbar to 650 mbar, and in step (b) the temperature is adjusted to 20° C. to 22° C. and the precipitated product is filtered off, preferably using a Nutsche filter, and the filter cake is washed with toluene, methanol, ethanol, isopropanol or n-propanol, particularly preferably with toluene.

In a particularly preferred embodiment of the present invention, the method for preparing isotianil includes the following steps of:

(a) reaction in an organic aprotic, preferably an aromatic, solvent, of
3,4-dichloroisothiazole-5-carbonyl chloride of the formula (II)

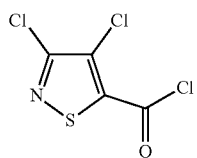

with 2-cyanoaniline (2-aminobenzonitrile) of the formula (III)

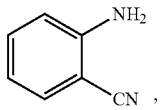

under reflux and optionally reduced pressure,
and
(b) filtration and washing,
in which the organic aprotic solvent is toluene, and
step (a) is carried out in a range from 70° C. to 90° C. and at 200 mbar to 450 mbar, and in step (b) the temperature is adjusted to 20° C. to 22° C., and the precipitated product is filtered off, preferably using a Nutsche filter, and the filter cake is washed with toluene, and the ratio of aminobenzonitrile to 3,4-dichloroisothiazole-5-carbonyl chloride is between 1:0.90 and 1:1.10, and the amount of solvent in kg in the ratio to the reactants in kmol is between 1000:1 and 150:1, and the reaction time (metered addition time plus further stirring time) is between 8 h and 2 h.

In the embodiments specified above, one reactant is preferably initially charged in the reaction regime and the second is metered into the reaction mixture by means of an immersed feed (immersion), wherein aminobenzonitrile is initially charged as a melt or can also be metered in. Preferably, the chloride is initially charged.

In the best embodiment of the present invention, the method for preparing isotianil accordingly includes the following steps of:

(a) reaction in an organic aprotic, preferably an aromatic, solvent, of
3,4-dichloroisothiazole-5-carbonyl chloride of the formula (II)

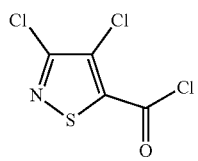

with 2-cyanoaniline (2-aminobenzonitrile) of the formula (III)

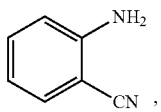

under reflux and optionally reduced pressure, wherein the aminobenzonitrile is added in the form of a melt or in solution, preferably in solution, by means of immersion,
and
(b) filtration and washing,
wherein the organic aprotic solvent selected is toluene, and
step (a) is carried out in a range from 70° C. to 90° C. and at 200 mbar to 450 mbar, and the ratio of aminobenzonitrile to 3,4-dichloroisothiazole-5-carbonyl chloride is between 1:0.95 and 1:1.04, and the amount of solvent in kg in the ratio to the reactants in kmol is between 826:1 and 238:1, and the reaction time (metered addition time plus further stirring time) is 6 h, and in step (b) the temperature is adjusted to 20° C. to 22° C., and the precipitated product is filtered off, preferably using a Nutsche filter, and the filter cake is washed with toluene.

The examples described below illustrate the present invention in more detail without being limited thereto.

SYNTHESIS AND COMPARATIVE EXAMPLES

Example 1 (Inventive): Initial Charge of Aminobenzonitrile in Toluene 59.2 g (0.5 mol, 99.8%) of aminobenzonitrile initially charged in 552.7 g (5.99 mol, 99.8%) of toluene. Over a period of 4 h at an internal temperature of 80° C. (bath temperature 100-114° C.) and 345 mbar (vigorous reflux), 114.4 g (0.48 mol, 90% in toluene) of DCIT chloride are added dropwise. Subsequently, the mixture is stirred under reflux at 80° C. and 345 mbar for 2 h. The reaction mixture was cooled to room temperature and filtered. The Nutsch cake was washed twice with methanol (displacement wash).

Yield: 98.8% of theory
Purity: 99.9%
Amount of waste: 1.6 kg/kg isotianil

Example 2 (Inventive): Initial Charge of DCIT Chloride in Toluene and Metered Addition of Aminobenzonitrile in Toluene 290.0 g (1.28 mol, 95.1% in toluene) of DCIT chloride and 51.9 g (0.56 mol, 100%) of toluene were initially charged. 145.3 g (1.23 mol, 100%) of aminobenzonitrile in 530.7 g (0.56 mol, 100%) in toluene are immersed dropwise over 4 h at an internal temperature of 80° C. (bath temperature 100-114° C.) and 345 mbar (vigorous reflux). Subsequently, the mixture is stirred under reflux at 80° C. and 345 mbar for 2 h. The reaction mixture was cooled to room temperature and filtered. The Nutsch cake was washed twice with toluene (displacement wash).

Isolated yield: 98.5% of theory (1.5% of theory in the mother liquor and filtrate wash) Purity: 99.8%
Amount of waste: 0.2 kg/kg isotianil Example 3 (Inventive): Initial Charge of DCIT Chloride in Toluene and Metered Addition of Aminobenzonitrile as a Melt 292.9 g (1.29 mol, 95.1% in toluene) of DCIT chloride and 475.8 g (5.16 mol, 100%) of toluene were initially charged at RT. 146.8 g (1.24 mol, 100%) of aminobenzonitrile as a melt are immersed dropwise over 4 h at an internal temperature of 80° C. (bath temperature 100-114° C.) and 350 mbar (vigorous reflux). Subsequently, the mixture is stirred under reflux at 80° C. and 345 mbar for 2 h. The reaction mixture was cooled to room temperature and filtered. The Nutsch cake was washed twice with toluene (displacement wash).

Isolated yield: 95.6% of theory (3.22% of theory in the mother liquor and filtrate wash)
Purity: 99.3%
Amount of waste: 0.2 kg/kg isotianil Example 4 (Inventive): Initial Charge of Aminobenzonitrile in Methyl Acetate as LM 59.2 g (0.5 mol, 99.8%) of aminobenzonitrile initially charged in 444.3 g (5.99 mol, 99.8%) of methyl acetate. Over a period of 4 h at an internal temperature of 45-47° C. (bath temperature 88-85° C.) and 600-605 mbar (vigorous reflux), 126.8 g (0.48 mol, 81.2% in methyl acetate) of DCIT chloride are added dropwise. Subsequently, the mixture is stirred under reflux at 45-47° C. and 600-605 mbar for 2 h. The reaction mixture was cooled to room temperature and filtered. The Nutsch cake was washed twice with methanol (displacement wash).

Yield: 94.2% of theory (1.22% of theory in the mother liquor and filtrate wash) Purity: 100%
Amount of waste: 0.3 kg/kg isotianil Example 5 (Inventive): Initial Charge of Aminobenzonitrile in Chlorobenzene as LM 59.19 g (0.5 mol, 99.8%) of aminobenzonitrile initially charged in 675.14 g (5.99 mol, 99.8%) of chlorobenzene. Over a period of 4 h at an internal temperature of 79-80° C. (bath temperature 101-102° C.) and 155-165 mbar (vigorous reflux), 126.8 g (0.48 mol, 81.2% in chlorobenzene) of DCIT chloride are added dropwise. Subsequently, the mixture is stirred under reflux at 79-80° C. and 155-170 mbar for 2 h. The reaction mixture was cooled to room temperature and filtered. The Nutsch cake was washed twice with methanol (displacement wash).

Yield: 92.0% of theory (4.6% of theory in the mother liquor and filtrate wash)
Purity: 100%
Amount of waste: 0.4 kg/kg isotianil Example 6 (Inventive): Initial Charge of Aminobenzonitrile in di-n-butyl Ether as LM 47.4 g (0.4 mol, 99.8%) of aminobenzonitrile initially charged in 624.9 g (4.79 mol, 99.8%) of di-n-butyl ether. Over a period of 4 h at an internal temperature of 79-80° C. (bath temperature 101-102° C.) and 105 mbar (vigorous reflux), 101.5 g (0.38 mol, 81.2% in di-n-butyl ether) of DCIT chloride are added dropwise. Subsequently, the mixture is stirred under reflux at 79-80° C. and 105 mbar for 2 h. The reaction mixture was cooled to room temperature and filtered. The Nutsch cake was washed twice with methanol (displacement wash).

Yield: 95.4% of theory (1.5% of theory in the mother liquor and filtrate wash)
Purity: 99.4%
Amount of waste: 0.4 kg/kg isotianil Example 7 (Inventive): Immersed Addition of 2-aminobenzonitrile as a Solution in Toluene 290 g (1.27 mol, 95.1%) of DCIT chloride and 46 g (0.5 mol, 100%) of toluene are initially charged at room temperature and heated to 80° C. A solution of 530.55 g (5.76 mol, 100%) of toluene and 145.34 g (1.23 mol, 99.8%) of aminobenzonitrile are metered in via immersion over 4 h at an internal temperature of 79-80° C. (bath temperature 101-102° C.) and 105 mbar (vigorous reflux). Subsequently, the mixture is stirred under reflux at 79-80° C. and 100-110 mbar for 2 h. The suspension is cooled to 20° C., filtered and washed twice with toluene.

Yield: 97.5% of theory (1.50% of theory in the mother liquor and filtrate wash)
Purity: 99.8%
Amount of waste: 0.2 kg/kg isotianil Comparative Example (Aminobenzonitrile Method)

To a mixture of 20.8 g (0.1725 mol) of 2-cyanoaniline and 250 ml of pyridine are added dropwise, at 5 to 10° C. with stirring, 38.1 g (0.15 mol) of 3,4-dichloroisothiazole-5-carbonyl chloride over a period of 10 minutes. After addition is complete, 70 ml of absolute tetrahydrofuran and 30 ml of pyridine are added, the mixture is allowed to warm to room temperature and then is stirred at room temperature for 75 minutes. Subsequently, the reaction mixture is concentrated under reduced pressure. The remaining residue is stirred with 800 ml of water and 800 ml of ethyl acetate. The precipitate obtained in the biphasic mixture is filtered off, washed with ethyl acetate and dried. In this manner, 31.7 g of a crystalline product of melting point 191 to 193° C. is obtained.

The aqueous phase is separated from the biphasic filtrate and extracted twice with 150 ml of ethyl acetate each time. The combined organic phases are dried over sodium sulfate and then concentrated under reduced pressure. The remaining residue is washed with 100 ml of petroleum ether and 25 ml of ethyl acetate and dried.

In this manner, a total of 40 g (89% of theory) of 3,4-dichloroisothiazole-5-carboxylic acid (2-cyanoanilide) is obtained in the form of a solid substance of melting point 191 to 193° C.

Isolated yield: 89% of theory
Amount of waste: 27.5 kg/kg isotianil
The invention claimed is:

1. Method for preparing isotianil comprising
(a) reacting in an organic aprotic solvent selected from the group consisting of benzene, toluene, o-xylene, m-xylene and p-xylene
3,4-dichloroisothiazole-5-carbonyl chloride of formula (II)

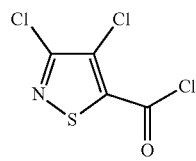

(II)

with 2-cyanoaniline (2-aminobenzonitrile) of formula (III)

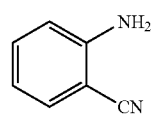

(III)

under reflux and optionally reduced pressure, and
(b) filtering and washing,
wherein in (a) optionally one of the reactants is initially charged in the solvent and heated, and the second reactant is subsequently metered in and wherein (a) is conducted in a range from 40° C. to 120° C. and at 150 mbar to 650 mbar.

2. Method according to claim 1, wherein in (b) the temperature is adjusted to 20° C. to 22° C. and a precipitated product is filtered off and a filter cake is washed with toluene, methanol, ethanol, isopropanol or n-propanol.

3. Method according to claim 1, wherein a reagent is added in the form of a melt or in solution by immersion.

4. Method according to claim 3, wherein 2-aminobenzonitrile is added in the form of a melt or in solution by immersion.

5. Method according to claim 1, wherein
(a) is carried out in a range from 40° C. to 120° C. and at 150 mbar to 650 mbar, and
in (b) the temperature is adjusted to 20° C. to 22° C. and a precipitated product is filtered off and a filter cake is washed with toluene, methanol, ethanol, isopropanol or n-propanol.

6. Method according to claim 1 wherein the organic aprotic solvent is toluene, and
(a) is carried out in a range from 70° C. to 90° C. and at 200 mbar to 450 mbar, and
in (b) the temperature is adjusted to 20° C. to 22° C., and the precipitated product is filtered off and the filter cake is washed with toluene,
and the ratio of 2-aminobenzonitrile to 3,4-dichloroisothiazole-5-carbonyl chloride is between 1:0.90 and 1:1.10, and
the amount of solvent in kg in the ratio to reactants in kmol is between 1000:1 and 150:1, and
reaction time (metered addition time plus further stirring time) is between 8 h and 2 h.

7. Method according to claim 1 wherein a reagent is added in the form of a melt or in solution by immersion,
and the organic aprotic solvent is toluene, and
(a) is carried out in a range from 70° C. to 90° C. and at 200 mbar to 450 mbar, and
the ratio of 2-aminobenzonitrile to 3,4-dichloroisothiazole-5-carbonyl chloride is between 1:0.95 and 1:1.04, and
the amount of solvent in kg in the ratio to reactants in kmol is between 826:1 and 238:1, and
reaction time (metered addition time plus further stirring time) is 6 h, and
in (b) the temperature is adjusted to 20° C. to 22° C., and a precipitated product is filtered off and a filter cake is washed with toluene.

8. Method according to claim 7, wherein 2-aminobenzonitrile is added in the form of a melt or in solution by immersion,
and the organic aprotic solvent is toluene, and
(a) is carried out in a range from 70° C. to 90° C. and at 200 mbar to 450 mbar, and
the ratio of 2-aminobenzonitrile to 3,4-dichloroisothiazole-5-carbonyl chloride is between 1:0.95 and 1:1.04, and
the amount of solvent in kg in the ratio to reactants in kmol is between 826:1 and 238:1, and
reaction time (metered addition time plus further stirring time) is 6 h, and
in (b) the temperature is adjusted to 20° C. to 22° C., and the precipitated product is filtered off and the filter cake is washed with toluene.

9. Method according to claim 7, wherein 2-aminobenzonitrile is added in solution by immersion,
and the organic aprotic solvent is toluene, and
(a) is carried out in a range from 70° C. to 90° C. and at 200 mbar to 450 mbar, and
the ratio of 2-aminobenzonitrile to 3,4-dichloroisothiazole-5-carbonyl chloride is between 1:0.95 and 1:1.04, and
the amount of solvent in kg in the ratio to reactants in kmol is between 826:1 and 238:1, and
reaction time (metered addition time plus further stirring time) is 6 h, and
in (b) the temperature is adjusted to 20° C. to 22° C., and the precipitated product is filtered off and the filter cake is washed with toluene.

10. The method according to claim 2 wherein the filtering is done using a Nutsche filter.

11. The method according to claim 5 wherein the filtering is done using a Nutsche filter.

12. The method according to claim 6 wherein the filtering is done using a Nutsche filter.

13. The method according to claim 7 wherein the filtering is done using a Nutsche filter.

14. The method according to claim 8 wherein the filtering is done using a Nutsche filter.

15. The method according to claim 9 wherein the filtering is done using a Nutsche filter.

* * * * *